United States Patent
Matsuura (10) Patent No.: US 9,810,621 B2
(45) Date of Patent: Nov. 7, 2017

(54) SAMPLE ANALYZER AND METHOD FOR REPLACING LIGHT SOURCE UNIT

(71) Applicant: Sysmex Corporation, Kobe-shi, Hyogo (JP)

(72) Inventor: Hiroyuki Matsuura, Kobe (JP)

(73) Assignee: Sysmex Corporation (JP)

( * ) Notice: Subject to any disclaimer, the term of this patent is extended or adjusted under 35 U.S.C. 154(b) by 166 days.

(21) Appl. No.: 14/836,222

(22) Filed: Aug. 26, 2015

(65) Prior Publication Data
US 2016/0061714 A1    Mar. 3, 2016

(30) Foreign Application Priority Data
Aug. 27, 2014  (JP) ................. 2014-172508

(51) Int. Cl.
| | | |
|---|---|---|
| G01N 21/00 | (2006.01) | |
| G01N 21/01 | (2006.01) | |
| G01N 35/04 | (2006.01) | |
| G01N 35/00 | (2006.01) | |

(52) U.S. Cl.
CPC ............. *G01N 21/01* (2013.01); *G01N 35/04* (2013.01); *G01N 2035/00306* (2013.01); *G01N 2035/00326* (2013.01); *G01N 2035/0415* (2013.01)

(58) Field of Classification Search
CPC .......... G01N 21/01; G01N 2021/0118; G01N 2035/00801; G01N 2035/026
See application file for complete search history.

(56) References Cited

U.S. PATENT DOCUMENTS

| | | |
|---|---|---|
| 5,506,679 A | 4/1996 | Cooper et al. |
| 2010/0159603 A1* | 6/2010 | Hamada ................. G01N 35/00 436/47 |
| 2010/0243916 A1 | 9/2010 | Maurer et al. |
| 2010/0248292 A1* | 9/2010 | Kuwano ................ G01N 35/02 435/29 |
| 2010/0290952 A1 | 11/2010 | Koike et al. |
| 2010/0330609 A1* | 12/2010 | Nagai ................ G01N 35/0092 435/29 |
| 2013/0160533 A1* | 6/2013 | Fukuma ................ G01N 35/00 73/64.56 |
| 2014/0256050 A1* | 9/2014 | Tanaka ................ G01N 35/026 436/47 |

FOREIGN PATENT DOCUMENTS

| | | |
|---|---|---|
| EP | 0 565 696 B1 | 10/1993 |
| EP | 2 256 502 A1 | 12/2010 |

* cited by examiner

*Primary Examiner* — Abdullahi Nur
(74) *Attorney, Agent, or Firm* — Brinks Gilson & Lione (57) ABSTRACT

Disclosed is a sample analyzer including: a transport apparatus configured to transport a sample rack holding a sample container; and a measurement apparatus body configured to measure a sample in the sample container held in the sample rack transported by the transport apparatus, wherein the transport apparatus includes a light source holding unit configured to detachably hold a light source unit, and the measurement apparatus body includes a detection unit configured to detect, via an analysis specimen containing the sample, light emitted from the light source unit held in the light source holding unit.

16 Claims, 5 Drawing Sheets

SAMPLE ANALYZER AND METHOD FOR REPLACING LIGHT SOURCE UNIT

CROSS REFERENCE TO RELATED APPLICATIONS

This application claims priority from prior Japanese Patent Application No. 2014-172508, filed on Aug. 27, 2014, entitled "SAMPLE ANALYZER", the entire content of which is incorporated herein by reference.

FIELD OF THE INVENTION

The present invention relates to sample analyzers.

BACKGROUND

There are sample analyzers equipped with light source units (for example, see US Patent Publication No. 2010/0290952).

US Patent Publication No. 2010/0290952 discloses a sample analyzer including: a transport mechanism unit configured to transport a rack which holds sample containers; and a detection mechanism unit body configured to perform optical measurement on samples supplied from the transport mechanism unit. The transport mechanism unit is provided on the front face side of the detection mechanism unit body. The detection mechanism unit body includes a housing. In the housing, provided are a light source unit, a light source holding unit which detachably holds the light source unit, and a detection unit which detects light emitted from the light source unit via an analysis specimen which contains a sample. The housing includes an opening which is open to a lateral side. The light source unit is replaced by a user through the opening.

SUMMARY OF THE INVENTION

The scope of the present invention is defined solely by the appended claims, and is not affected to any degree by the statements within this summary.

A sample analyzer according to a first aspect of the present invention includes: a transport apparatus configured to transport a sample rack holding a sample container; and a measurement apparatus body configured to measure a sample in the sample container held in the sample rack transported by the transport apparatus. The transport apparatus includes a light source holding unit configured to detachably hold a light source unit, and the measurement apparatus body includes a detection unit configured to detect, via an analysis specimen containing the sample, light emitted from the light source unit held in the light source holding unit.

A sample analyzer according to a second aspect of the present invention includes: a measurement apparatus body configured to measure a sample and having an operation panel disposed thereon; and a housing having a light source holding unit configured to detachably hold a light source unit and provided adjacent to the measurement apparatus body on a side where the operation panel is disposed, wherein the measurement apparatus body includes a detection unit configured to detect, via an analysis specimen containing the sample, light emitted from the light source unit held in the light source holding unit.

A method for replacing a light source unit of a sample analyzer according to a third aspect of the present invention includes: the sample analyzer including: a transport apparatus configured to transport a sample rack holding a sample container; and a measurement apparatus body configured to measure a sample in the sample container held in the sample rack transported by the transport apparatus, wherein the method including: dismounting a cover included in the transport apparatus; and replacing the light source unit held in a light source holding unit included in the transport apparatus through an opening uncovered by dismounting the cover.

DETAILED DESCRIPTION OF THE PREFERRED EMBODIMENTS

Hereinafter, with reference to FIG. 1 to FIG. 5, a configuration of a sample analyzer 10 according to one embodiment will be described.

Figure 1:
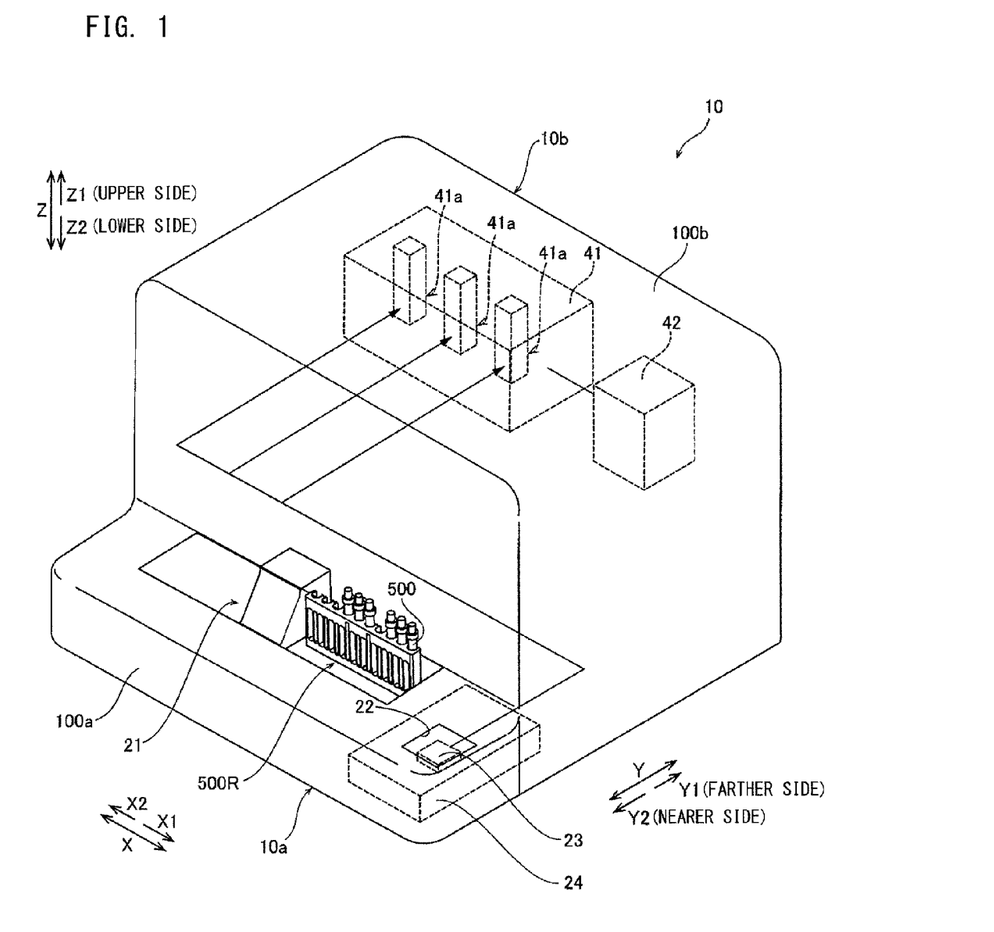
FIG. 1 is a schematic diagram showing a sample analyzer according to one embodiment.

The sample analyzer 10 shown in FIG. 1 is an apparatus for performing optical measurement on an analysis specimen (hereinafter, referred to as specimen) prepared by mixing a sample and a reagent. The sample analyzer 10 performs analysis of components of the sample based on optical information obtained from the measurement.

The sample analyzer 10 is composed of a transport apparatus 10a and a measurement apparatus body 10b. The sample analyzer 10 has the transport apparatus 10a on the Y2 side, and the measurement apparatus body 10b on the Y1 side. The transport apparatus 10a transports a sample rack 500R holding sample containers 500. The measurement apparatus body 10b measures the sample in each sample container 500 held in the sample rack 500R having been transported by the transport apparatus 10a. Herein, the "nearer side" refers to the front side (Y2 side) of the sample analyzer 10 which has been installed. The "farther side" means the opposite side (Y1 side) to the nearer side of the sample analyzer 10.

First, a connection state of the transport apparatus 10a and the measurement apparatus body 10b will be described. Thereafter, details of the transport apparatus 10a and the measurement apparatus body 10b will be described.

Figure 2:
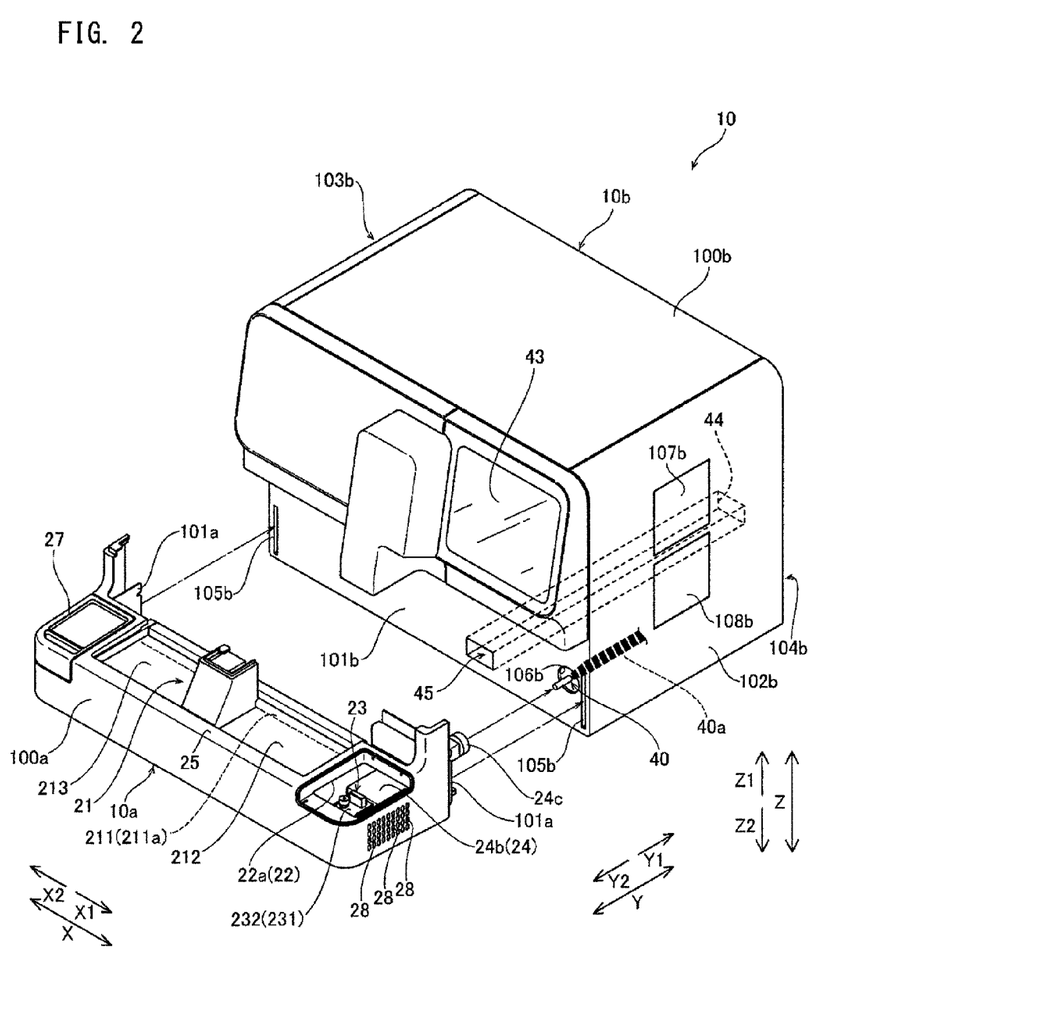
FIG. 2 shows a state where a transport apparatus and a measurement apparatus body of the sample analyzer are connected to each other according to one embodiment.

As shown in FIG. 2, the transport apparatus 10a includes a transport apparatus housing 100a. The transport apparatus housing 100a is a case member of the transport apparatus 10a. The transport apparatus housing 100a includes a pair of engagement parts 101a. The engagement parts 101a are at the Y1 side end of the transport apparatus housing 100a. The engagement parts 101a are at both end portions in the X direction of the transport apparatus housing 100a, respectively.

The measurement apparatus body 10b includes a front face 101b, a first lateral face 102b, a second lateral face 103b, and a farther-side face 104b. The measurement apparatus body 10b includes a measurement apparatus housing 100b. The measurement apparatus housing 100b is a case member of the measurement apparatus body 10b. The front face 101b, the first lateral face 102b, the second lateral face 103b, and the farther-side face 104b are respectively the faces that extend vertically and surround the measurement apparatus housing 100b.

The transport apparatus 10a is adjacent to the front face 101b. The front face 101b is the face on the Y2 side of the measurement apparatus housing 100b. The front face 101b is at a lower part of the measurement apparatus housing 100b. The front face 101b is substantially parallel to the X direction. The front face 101b is formed in a flat shape. The front face 101b is provided with a pair of engagement parts 105b. The engagement parts 105b are at the Y2 side end of the measurement apparatus body 10b. The engagement parts 105b are at both end portions in the X direction of the measurement apparatus body 10b, respectively. The transport apparatus 10a is mounted to the measurement apparatus body 10b, with the engagement parts 101a respectively engaged with the engagement parts 105b of the measurement apparatus body 10b described later.

Preferably, the front face 101b has a hole 106b on the side (Y2 side) thereof to which the transport apparatus 10a is adjacent. The hole 106b is a through-hole.

The first lateral face 102b is the lateral face on the X1 side of the measurement apparatus housing 100b. The first lateral face 102b crosses the front face 101b. The first lateral face 102b has a cuvette supply hole 107b. The first lateral face 102b has a cuvette discharge hole 108b.

The second lateral face 103b is the lateral face on the X2 side of the measurement apparatus housing 100b. The second lateral face 103b crosses the front face 101b. The first lateral face 102b and the second lateral face 103b are each orthogonal to the front face 101b.

The farther-side face 104b is the face on the Y1 side of the measurement apparatus housing 100b. The farther-side face 104b is substantially parallel to the X direction.

Now, details of the transport apparatus 10a and the measurement apparatus body 10b will be described below.

Figure 3:
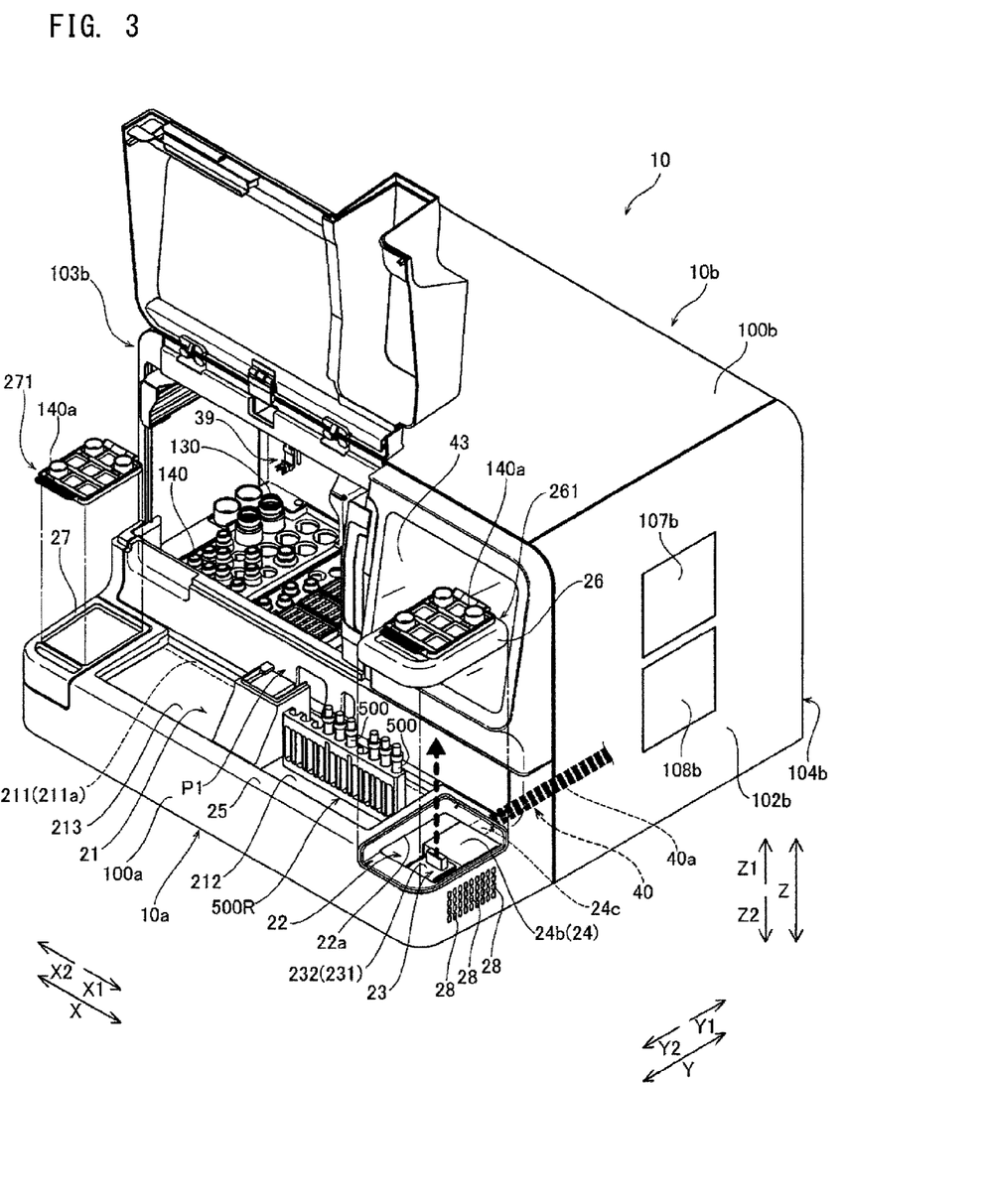
FIG. 3 is a perspective view showing the sample analyzer according to one embodiment.
Figure 4:
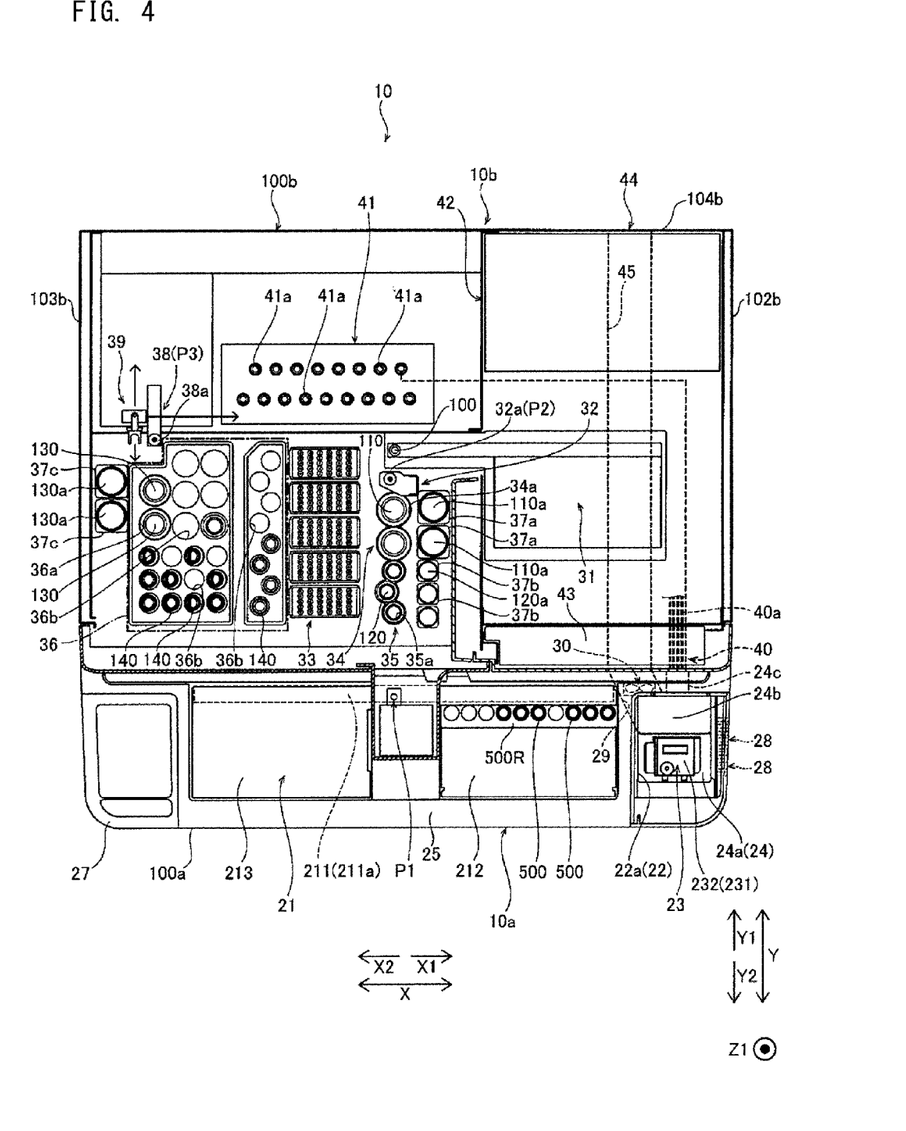
FIG. 4 is a plan view showing the inside of the sample analyzer according to one embodiment.

As shown in FIG. 3, the transport apparatus 10a includes a transport mechanism 21, an opening 22, a light source unit 23, a light source holding unit 24, a protruding part 25, and a plurality of covers 26 and 27. The transport apparatus 10a includes a plurality of air intake holes 28, an air guide path 29 (see FIG. 4), and a fan 30 (see FIG. 4). As shown in FIG. 4, the measurement apparatus body 10b includes a cuvette supply unit 31, a sample dispenser 32, a sample plate placement part 33, container setting parts 34 to 36, and cap placement parts 37a to 37c. The measurement apparatus body 10b includes a reagent dispenser 38, a cuvette transfer unit 39, and an optical fiber 40. The measurement apparatus body 10b includes a detection unit 41, an analysis unit 42, an operation panel 43, an air outlet 44, and an air guide path 45.

With reference back to FIG. 3, the transport mechanism 21 is provided on the upper face of the transport apparatus 10a. The transport mechanism 21 includes a rack transporter 211, a rack supplier 212, and a rack storage 213. The transport mechanism 21 has a function of transporting a sample rack 500R.

The rack transporter 211 extends in the X direction. The rack transporter 211 includes a placement face 211a on which to place a sample container 500. On the placement face 211a, a sample rack 500R holding sample containers 500 can be placed. The rack transporter 211 can transport the sample rack 500R set in the rack supplier 212. The rack transporter 211 connects the rack supplier 212 and the rack storage 213 which is on the X2 direction side.

Preferably, the rack supplier 212 is disposed on the first lateral face 102b side (X1 side). In the rack supplier 212, sample racks 500R each holding sample containers 500 are set. The rack supplier 212 can sequentially set a sample rack 500R onto the rack transporter 211. The rack transporter 211 can transport the sample rack 500R set by the rack supplier 212, to a sample aspirating position P1.

The rack storage 213 can receive, from the rack transporter 211, the sample rack 500R holding sample containers 500 from which the samples have been aspirated. The rack storage 213 can store the sample rack 500R therein.

Preferably, the opening 22 is provided in the transport apparatus 10a so as to be open to the upper side (Z1 side). That is, the opening 22 is provided in the transport apparatus housing 100a so as to be open to the upper side. The opening 22 allows the light source unit 23 to be exposed to the upper side. The opening 22 is provided so as to allow the light source unit 23 to be taken in and out therethrough. Thus, it is possible to prevent the upper side relative to the light source unit 23 and relative to the light source holding unit 24 from being covered by the transport apparatus 10a. As a result, ambient light from the upper side can easily reach the light source unit 23 and the light source holding unit 24. Accordingly, when replacing the light source unit 23, the user can easily view the light source unit 23 and the light source holding unit 24, and thus, complicated work of replacing the light source unit 23 can be prevented. It should be noted that the opening 22 may be provided in a housing other than the transport apparatus 10a and the measurement apparatus body 10b.

The shape of the opening 22 is rectangular in a plan view (see FIG. 4). Preferably, the opening 22 is disposed so as to be adjacent to the first lateral face 102b side (X1 side) of the rack supplier 212. Accordingly, the user can collectively perform the work of replacing the light source unit 23 and the work of setting the sample rack 500R onto the rack supplier 212, at the X1 side of the analyzer. It should be noted that the opening 22 may be on the X2 side of the transport mechanism 21.

The opening 22 is provided on the Y2 side relative to the detection unit 41 (see FIG. 4) of the measurement apparatus body 10b. Accordingly, unlike the case where the opening 22 is provided in a farther-side portion of the sample analyzer 10, the light source unit 23 can be easily taken in and out through the opening 22 which is provided on the nearer side (Y2 side). The opening 22 can be provided on the nearer side (Y2 side), not in a farther-side portion of the sample analyzer 10. Accordingly, ambient light from the upper side can be prevented from being blocked by the transport apparatus 10a of the sample analyzer 10. As a result, ambient light from the upper side can further easily reach the light source unit 23 and the light source holding unit 24.

Preferably, an upper edge 22a of the opening 22 is provided at a level substantially identical to that of the placement face 211a. Specifically, the upper edge 22a is at a level substantially identical to that of the placement face 211a of the transport mechanism 21. Accordingly, unlike the case where the upper edge 22a of the opening 22 is provided at a lower level than the placement face 211a, even when liquid is spilt onto the placement face 211a during sample analysis operation, the spilt liquid is less likely to reach the light source unit 23.

Preferably, the opening 22 is formed so as to overlap the light source holding unit 24 in a plan view. Accordingly, the light source unit 23 can be easily taken into and out of the light source holding unit 24.

Preferably, the opening 22 has an area larger than the area of the light source unit 23 in a plan view. In addition, the opening 22 has an area larger than the area of a housing 232 described later, in a plan view. Accordingly, when the light source unit 23 is to be taken into and out of the light source holding unit 24, interference between the housing 232 and the opening 22 can be prevented.

As shown in FIG. 4, preferably, the opening 22 overlaps the rack transporter 211, when viewed in the X direction. That is, the position in the Y direction of the opening 22 overlaps the position in the Y direction of the rack transporter 211. Accordingly, unlike the case where the opening 22 does not overlap the rack transporter 211 when viewed in the X direction, the portion of the opening 22 projecting relative to the rack transporter 211 in the front-rear direction (Y direction) can be reduced. As a result, the outer shape of the sample analyzer 10 can be compact.

Figure 5:
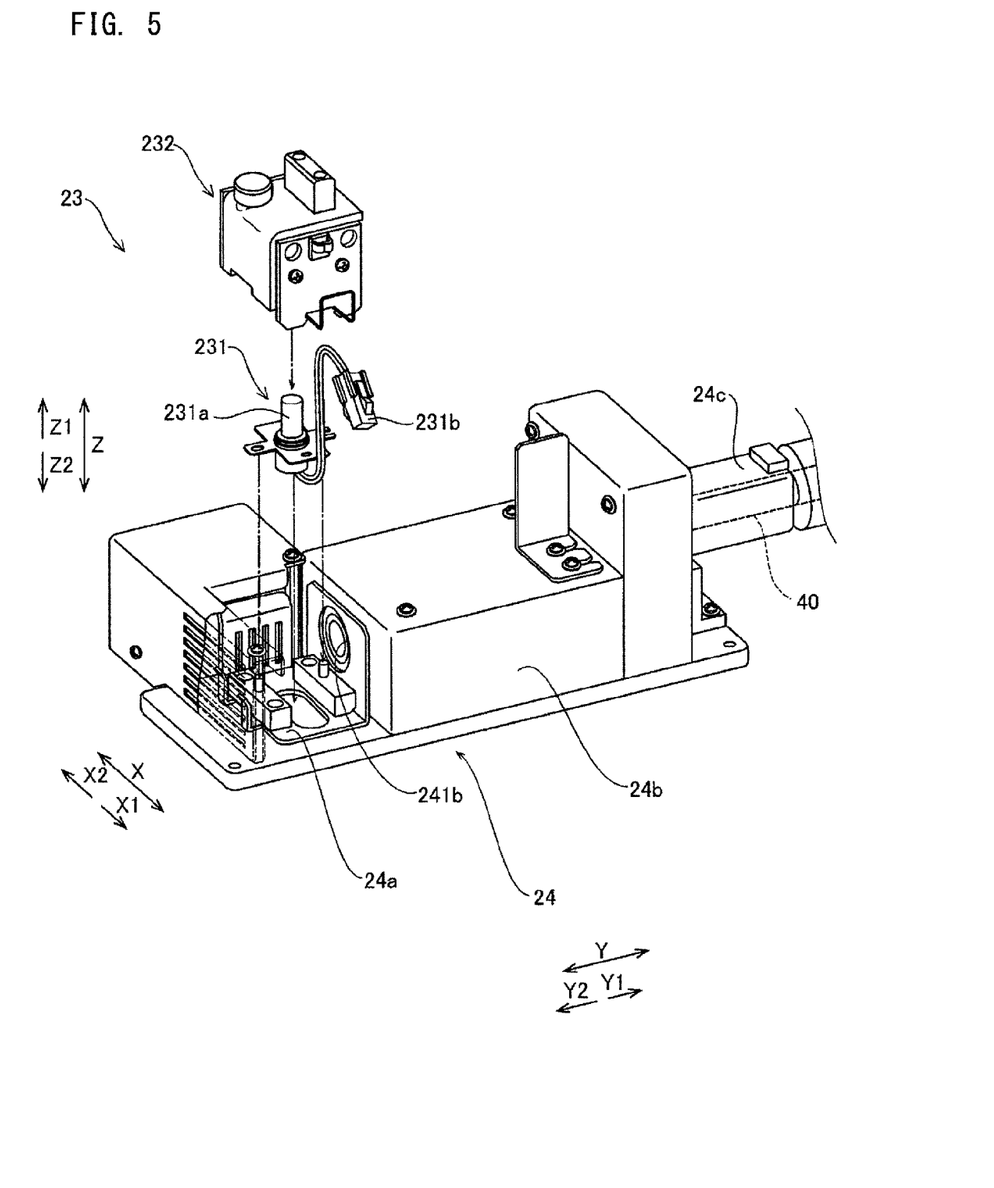
FIG. 5 is a perspective view showing a light source unit and a light source holding unit of the sample analyzer according to one embodiment.

As shown in FIG. 5, the light source unit 23 includes a light source 231, and the housing 232 which covers the light source 231. Accordingly, the upper side relative to the light source 231 can be protected by the housing 232. It should be noted that the light source unit 23 may not include the housing 232.

The light source unit 23 is accommodated below the opening 22 (see FIG. 3). The light source unit 23 can be taken into and out of the transport apparatus 10a (see FIG. 3) through the opening 22. The light source unit 23 is held by the light source holding unit 24 so as to be detachable therefrom.

With reference back to FIG. 4, preferably, the transport apparatus 10a is disposed adjacent to the measurement apparatus body 10b. Specifically, the transport apparatus 10a is placed on the Y2 side of the measurement apparatus body 10b. Accordingly, the light source unit 23 can be disposed near to the detection unit 41. When light emitted from the light source unit 23 is supplied to the detection unit 41, loss of the light in the course of the transmission can be suppressed. The transport apparatus housing 100a includes the light source holding unit 24 which detachably holds the light source unit 23. In addition, the transport apparatus housing 100a is placed adjacent to the measurement apparatus body 10b, on the side (nearer side) where the operation panel 43 is disposed. It should be noted that a housing different from the transport apparatus housing 100a may be disposed adjacent to the measurement apparatus body 10b.

With reference back to FIG. 5, preferably, the light source 231 includes a light-emitting device such as a halogen lamp 231a. Accordingly, the light source 231 can be configured to be compact. It should be noted that the light source 231 may include a light source other than the halogen lamp 231a, such as laser light source, for example.

A wire 231b of the light source 231 is connected to a connector not shown.

The housing 232 is made of metal such as aluminium. The housing 232 houses the light source 231, while covering it from above.

In a state where the housing 232 is held in the light source holding unit 24, the level of the top of the housing 232 is lower than the level of the upper edge 22a of the opening 22 (see FIG. 3).

The light source holding unit 24 fixes the light source unit 23 in a light source holding region 24a. The light source holding unit 24 includes a case part 24b. The case part 24b houses a condenser lens and a filter member not shown. The case part 24b includes a connection part 24c on the Y1 side. The connection part 24c is at a position corresponding to the hole 106b (see FIG. 2) in the front face 101b of the measurement apparatus body 10b. The connection part 24c is connected to the optical fiber 40. Light emitted from the light source 231 is guided into the case part 24b via a hole part 241b of the case part 24b. Then, this light is guided to the optical fiber 40, via the condenser lens and the filter member not shown. The filter member includes a plurality of filters having different transmission wavelengths. The filter member can supply light having a plurality of different wavelengths to the optical fiber 40.

Preferably, the light source holding unit 24 is configured to allow the light source unit 23 to be dismounted toward the upper side (Z1 direction) through the opening 22 (see FIG. 3). Thus, the work of replacing the light source unit 23 can be easily performed.

Preferably, the light source holding unit 24 is disposed adjacent to the rack supplier 212. Specifically, the light source holding unit 24 is provided outside, on the X1 side, of the transport mechanism 21. Accordingly, the light source unit 23 can be disposed at a location distanced from the location where cleaning liquid containers 110 (see FIG. 4), diluent containers 120 (see FIG. 4), cleaning liquid containers 130, and reagent containers 140 described later (hereinafter, the cleaning liquid containers 110, the diluent containers 120, the cleaning liquid containers 130, and the reagent containers 140 are collectively referred to as "liquid containers") are disposed. It should be noted that the light source holding unit 24 may be disposed adjacent to the rack storage 213.

With reference back to FIG. 3, the protruding part 25 is provided outside the transport mechanism 21. The protruding part 25 is provided so as to surround the transport mechanism 21 from the X1 side, the X2 side, and the Y2 side. The protruding part 25 protrudes further to the upper side than the upper edge 22a of the opening 22 and the transport mechanism 21. The transport mechanism 21 and the opening 22 are provided so as to be separated from each other via the protruding part 25.

The covers 26 and 27 are disposed on the X1 side and the X2 side of the transport apparatus 10a, respectively. Specifically, the covers 26 and 27 are disposed so as to sandwich the transport mechanism 21 from both sides in the X direction.

Preferably, the opening 22 is formed such that the upper side relative to itself can be covered by the cover 26. A cap placement part 261 on which to place caps 140a of reagent containers 140 can be placed on the upper face of the cover 26. Specifically, the upper face of the cover 26 is formed in a recessed shape which allows the cap placement part 261 to be placed thereon. Accordingly, the space above the cover 26 can be effectively used by disposing the cap placement part 261 on the cover 26 while the upper side relative to the light source unit 23 is protected by the cover 26.

Similarly to the cover 26, a cap placement part 271 on which to place caps 140a of reagent containers 140 can be placed on the upper face of the cover 27.

The cap placement parts 261 and 271 are respectively engaged with the upper faces of the covers 26 and 27 each formed in a recessed shape. Thus, the cap placement parts 261 and 271 can be respectively disposed on the upper faces of the covers 26 and 27 so as not to be displaced therefrom. The cap placement parts 261 and 271 can have caps 140a of reagent containers 140 placed thereon. The cap placement parts 261 and 271 are each divided into a plurality of grid-shaped sections.

The plurality of air intake holes 28 are provided on the X1 side of the transport apparatus 10*a*. Each air intake hole 28 is a through-hole. As shown in FIG. 4, the plurality of air intake holes 28 overlap the opening 22, when viewed in the X direction. The air intake holes 28 allow air to be taken into the transport apparatus 10*a* from outside thereof. In the vicinity on the X2 side of air intake holes 28, the light source unit 23 is provided.

The air guide path 29 is a through-hole extending from a position in the vicinity of the light source unit 23 toward the farther side (Y1 side).

The fan 30 is provided in the air guide path 29, in the vicinity of the light source unit 23. The fan 30 sends air in the air guide path 29 from the Y2 side toward the Y1 side.

The cuvette supply unit 31 contains a plurality of cuvettes 100. The cuvette supply unit 31 can supply cuvettes 100 one by one to a predetermined position. New cuvettes 100 are provided to the cuvette supply unit 31 via the cuvette supply hole 107*b* (see FIG. 3). Used cuvettes 100 are taken out from the inside of the sample analyzer 10 via the cuvette discharge hole 108*b* (see FIG. 3).

The sample dispenser 32 is equipped with a pipette 32*a*. The pipette 32*a* can aspirate and discharge a sample. The sample dispenser 32 can move in a region including the sample aspirating position P1 and a sample dispensing position P2, by means of a movement mechanism not shown. The sample dispenser 32 dispenses the sample contained in a sample container 500 having been transported to the sample aspirating position P1 of the transport apparatus 10*a*, into a cuvette 100 disposed at the sample dispensing position P2. The sample dispenser 32 aspirates a cleaning liquid from a cleaning liquid container 110 set in the container setting part 34. The sample dispenser 32 aspirates a diluent from a diluent container 120 set in the container setting part 35.

In the sample plate placement part 33, sample plates having a plurality of holes are placed side by side. In the case where a plurality of specimens are to be prepared for one sample in accordance with its analysis items, the sample dispenser 32 can collectively perform sample dispensing for the analysis items in the sample plate placement part 33.

The container setting part 34 is provided in a center portion in the X direction of the analyzer. The container setting part 34 includes two setting holes 34*a* in which cleaning liquid containers 110 can be respectively set. With the cleaning liquid in the cleaning liquid container 110, the pipette 32*a* of the sample dispenser 32 is cleaned. In the vicinity of the container setting part 34, the cap placement part 37*a* is provided. In the cap placement part 37*a*, caps 110*a* of cleaning liquid containers 110 can be placed.

The container setting part 35 is provided in the center portion in the X direction of the analyzer. The container setting part 35 includes three setting holes 35*a* in which diluent containers 120 can be respectively set. In the vicinity of the container setting part 35, the cap placement part 37*b* is provided. In the cap placement part 37*b*, caps 120*a* of diluent containers 120 can be placed.

The container setting part 36 is provided on the X2 side of the analyzer. The container setting part 36 includes two setting hole 36*a* in which cleaning liquid containers 130 can be respectively set. The container setting part 36 includes a plurality of setting holes 36*b* in which reagent containers 140 can be respectively set. With the cleaning liquid in the cleaning liquid container 130, a pipette 38*a* of the reagent dispenser 38 is cleaned. The reagent containers 140 contain various types of reagents to be added when a specimen is to be prepared from a sample. In the vicinity of the container setting part 36, the cap placement part 37*c* is provided. In the cap placement part 37*c*, caps 130*a* of cleaning liquid containers 130 can be placed. The caps 140*a* of reagent containers 140 can be placed on the cap placement parts 261 and 271 (see FIG. 3) respectively disposed on the covers 26 and 27.

The reagent dispenser 38 is equipped with the pipette 38*a* which dispenses a reagent. The reagent dispenser 38 can move in a region including the upper side relative to the container setting part 36 and a reagent dispensing position P3, by means of a movement mechanism not shown. The reagent dispenser 38 aspirates a reagent from a reagent container 140 being the dispensing target, and dispenses the reagent into a cuvette 100 disposed at the reagent dispensing position P3. The reagent dispenser 38 aspirates a cleaning liquid from a cleaning liquid container 130 set in the container setting part 36.

The cuvette transfer unit 39 can hold the cuvette 100 having been supplied by the cuvette supply unit 31. The cuvette transfer unit 39 can transfer the cuvette 100 to the sample dispensing position P2, the reagent dispensing position P3, the detection unit 41, and the like. The cuvette transfer unit 39 can also agitate the sample and the reagent in the cuvette 100.

Preferably, the optical fiber 40 connects the light source unit 23 and the detection unit 41. Accordingly, when light emitted from the light source unit 23 is supplied to the detection unit 41, loss of the light in the course of the transmission can be suppressed. As a result, the specimen can be analyzed accurately. It should be noted that the light source unit 23 and the detection unit 41 may be connected to each other by use of a light transmitting mechanism other than the optical fiber 40.

More preferably, the transport apparatus 10*a* is mounted to the measurement apparatus body 10*b*, in a state where the optical fiber 40 and the light source holding unit 24 are connected to each other via the hole 106*b* (see FIG. 2). Accordingly, the optical fiber 40 and the light source holding unit 24 can be easily connected to each other. As a result, when light emitted from the light source unit 23 is supplied to the detection unit 41, loss of the light in the course of the transmission is suppressed, and at the same time, the transport apparatus 10*a* and the measurement apparatus body 10*b* can be connected to each other.

The optical fiber 40 protrudes to the Y2 side from the measurement apparatus body 10*b* (see FIG. 2). The optical fiber 40 is connected to the connection part 24*c* of the light source holding unit 24, at the tip of the protruding portion of the optical fiber 40. It should be noted that the tip on the Y2 side of the optical fiber 40 may be positioned inside the measurement apparatus body 10*b*. In such a case, the optical fiber 40 is connected to the connection part 24*c* of the light source holding unit 24, inside the measurement apparatus body 10*b*.

The optical fiber 40 includes a plurality of branched optical fibers 40*a* on the Y1 side. The plurality of branched optical fibers 40*a* respectively supply light to cuvettes 100 disposed in a plurality of cuvette setting holes 41*a* in the detection unit 41.

FIG. 2 to FIG. 4 each show the optical fiber 40 in a simplified manner. For simplification, in FIG. 4, a state where one branched optical fiber 40*a* is connected to one cuvette setting hole 41*a* is shown, and a state where other branched optical fibers 40a are connected to other cuvette setting holes 4l a are not shown.

The detection unit 41 detects light emitted from the light source unit 23 held in the light source holding unit 24, via an analysis specimen which contains a sample. The detection unit 41 is provided on the Y1 side (farther side) relative to the light source unit 23. Specifically, the detection unit 41 is provided on the Y1 side relative to the center of the measurement apparatus body 10b in the Y direction. The detection unit 41 includes a plurality of cuvette setting holes 41a in which to set cuvettes 100. In the detection unit 41, light guided via the optical fiber 40 hits the specimen in each cuvette setting hole 41a. The detection unit 41 includes light receiving elements not shown which each receive light having hit its corresponding specimen. Accordingly, the detection unit 41 can detect, via each specimen, light emitted from the light source unit 23. The detection unit 41 outputs, to the analysis unit 42, a detection signal corresponding to the amount of light received by each light receiving element.

The analysis unit 42 analyzes the amount of a specific component in the sample or the degree of activity of a specific component in the sample, based on the detection signal obtained from the detection unit 41. The analysis unit 42 can display an analysis result and the like on the operation panel 43.

The operation panel 43 is provided on the Y2 side of the measurement apparatus body 10b. The operation panel 43 can display information regarding sample analysis. The operation panel 43 is a touch panel of a capacitance type, for example. Thus, the user can operate the sample analyzer 10 by inputting operation information onto the operation panel 43.

Preferably, the operation panel 43 is provided on the first lateral face 102b side (X1 side). Specifically, the operation panel 43 is provided on the X1 side relative to the center position in the X direction. Thus, the user can collectively perform, on the X1 side of the analyzer, the work of viewing information displayed on the operation panel 43, the work of inputting operation information onto the operation panel 43, and the work of replacing the light source unit 23.

The opening 22, the operation panel 43, the cuvette supply hole 107b (see FIG. 3), and the cuvette discharge hole 108b (see FIG. 3) are provided on the X1 side relative to the center position in the X direction. Accordingly, the user can collectively perform, on the X1 side of the analyzer, a series of maintenance work for the analyzer, such as viewing information displayed on the operation panel 43, inputting operation information onto the operation panel 43, replacing the light source unit 23, setting new cuvettes 100, taking out of used cuvettes 100, and setting a sample rack 500R on the rack supplier 212. As a result, the burden of work on the user relating to use of the sample analyzer 10 can be reduced.

Preferably, the air outlet 44 is formed on the farther side, of the measurement apparatus body 10b, which is the side (Y1 side) opposite to the side where the transport apparatus 10a is adjacent. Specifically, the air outlet 44 is provided on the Y1 side (farther side) of the measurement apparatus body 10b. The air outlet 44 is open in the farther-side face 104b of the measurement apparatus body 10b. The air outlet 44 allows air to be discharged from inside of the measurement apparatus body 10b to outside thereof.

The air guide path 45 is a through-hole extending along the Y direction.

Preferably, the air guide path 45 is connected to the air outlet 44, and guides heat released from the light source unit 23, to the air outlet 44. Specifically, with respect to the air guide path 45, the Y2 side thereof is connected to the air guide path 29 of the transport apparatus 10a, and the Y1 side thereof is connected to the air outlet 44. Accordingly, heat released from the light source unit 23 (air heated by the light source unit 23) is discharged to outside of the sample analyzer 10, by the fan 30 disposed in the air guide path 29, via the air guide paths 29 and 45 and the air outlet 44. As a result, heat released from the light source unit 23 is prevented from staying inside the analyzer. It should be noted that the sample analyzer 10 may not include the air guide paths 29 and 45, the fan 30, the air intake holes 28, and the air outlet 44.

According to the present embodiment, by providing a housing such as the transport apparatus housing 100a which includes the light source holding unit 24 and which is provided adjacent to the measurement apparatus body 10b on the side (nearer side) where the operation panel 43 is disposed, it is possible to replace the light source unit 23 on the side of the housing such as the transport apparatus housing 100a. Thus, unlike the configuration where the light source holding unit 24 is in the measurement apparatus body 10b, it is not necessary to replace the light source unit 23 via a lateral face portion or the like of the measurement apparatus body 10b. Accordingly, the work of replacing the light source unit 23 can be easily performed.

It should be noted that the embodiment disclosed herein is merely illustrative in all aspects and should not be considered as being restrictive. The scope of the present invention is not defined by the description of the above embodiment, but by the claims, and includes meaning equivalent to the claims and all modifications within the scope.

What is claimed is:

1. A sample analyzer comprising:
    a transport apparatus configured to transport a sample rack holding a sample container; and
    a measurement apparatus body configured to measure a sample in the sample container held in the sample rack transported by the transport apparatus, wherein
    the transport apparatus comprises a light source holding unit configured to detachably hold a light source unit, and
    the measurement apparatus body comprises a detection unit configured to detect, via an analysis specimen containing the sample, light emitted from the light source unit held in the light source holding unit;
    wherein the measurement apparatus body further comprises: a sample dispenser configured to dispense, into a cuvette, the sample contained in the sample container held in the sample rack transported by the transport apparatus; and a reagent dispenser configured to dispense a reagent into the cuvette, and
    the analysis specimen contains the sample and the reagent.

2. The sample analyzer of claim 1, wherein
    the transport apparatus is disposed adjacent to the measurement apparatus body.

3. The sample analyzer of claim 1, further comprising
    an optical fiber which connects the light source unit and the detection unit.

4. The sample analyzer of claim 3, wherein
    the transport apparatus is disposed adjacent to the measurement apparatus body,
    the measurement apparatus body comprises a front face which includes a hole on the side where the transport apparatus is adjacent, and the transport apparatus is mounted to the measurement apparatus body, in a state where the optical fiber and the light source holding unit are connected to each other via the hole.

5. The sample analyzer of claim 1, wherein the light source unit includes a halogen lamp.

6. The sample analyzer of claim 1, further comprising an analysis unit configured to analyze an amount of a component contained in the sample or a degree of activity of a component contained in the sample, based on a signal detected by the detection unit.

7. A sample analyzer comprising:
a transport apparatus configured to transport a sample rack holding a sample container; and
a measurement apparatus body configured to measure a sample in the sample container held in the sample rack transported by the transport apparatus, wherein
the transport apparatus comprises a light source holding unit configured to detachably hold a light source unit, and
the measurement apparatus body comprises a detection unit configured to detect, via an analysis specimen containing the sample, light emitted from the light source unit held in the light source holding unit
wherein
the transport apparatus comprises:
a rack supplier on which to set the sample rack;
a rack transporter configured to transport the sample rack set on the rack supplier; and
a rack storage in which to store the sample rack transported by the rack transporter, and
the light source holding unit is disposed adjacent to the rack supplier or the rack storage.

8. The sample analyzer of claim 7, wherein the transport apparatus has an opening which is open to an upper side and which allows the light source unit to be taken in and out therethrough.

9. The sample analyzer of claim 8, wherein
the transport apparatus is disposed adjacent to the measurement apparatus body,
the measurement apparatus body comprises a front face to which the transport apparatus is adjacent, and a lateral face which is substantially orthogonal to the front face, and
the opening is formed so as to overlap the rack transporter in a side view.

10. The sample analyzer of claim 8, wherein
the rack transporter includes a placement face on which to place the sample container, and
an upper edge of the opening is disposed at a level substantially identical to that of the placement face.

11. The sample analyzer of claim 8, wherein
the transport apparatus is disposed adjacent to the measurement apparatus body, and
the measurement apparatus body comprises a front face to which the transport apparatus is adjacent, and a first lateral face and a second lateral face which are substantially orthogonal to the front face,
the sample analyzer further comprises an operation panel disposed on the first lateral face side,
the rack supplier is disposed on the first lateral face side, and
the opening is disposed so as to be adjacent to the first lateral face side of the rack supplier.

12. The sample analyzer of claim 8, wherein
the light source holding unit is configured to allow the light source unit to be dismounted toward the upper side through the opening.

13. The sample analyzer according to claim 8, wherein
the opening is formed so as to overlap the light source holding unit in a plan view.

14. The sample analyzer of claim 13, wherein
the opening has an area larger than an area of the light source unit in a plan view.

15. The sample analyzer of claim 8, wherein
the transport apparatus has an opening which is open to the upper side and which allows the light source unit to be taken in and out therethrough,
the analysis specimen is prepared by mixing the sample and a reagent,
the reagent is contained in a reagent container,
the opening is formed such that the upper side relative to itself is covered by a cover, and
an upper face of the cover is configured to allow a cap placement part to be placed thereon, the cap placement part for placing a cap of the reagent container thereon.

16. A sample analyzer comprising:
a transport apparatus configured to transport a sample rack holding a sample container; and
a measurement apparatus body configured to measure a sample in the sample container held in the sample rack transported by the transport apparatus, wherein
the transport apparatus comprises a light source holding unit configured to detachably hold a light source unit, and
the measurement apparatus body comprises a detection unit configured to detect, via an analysis specimen containing the sample, light emitted from the light source unit held in the light source holding unit;
the transport apparatus is disposed adjacent to the measurement apparatus body;
wherein
the measurement apparatus body further comprises: an air outlet formed on a farther side thereof which is opposite to the side where the transport apparatus is adjacent, the air outlet for discharging air from inside of the measurement apparatus body to outside thereof; and an air guide path connected to the air outlet and for guiding heat released from the light source unit, to the air outlet.

* * * * *